(12) United States Patent
Rao et al.

(10) Patent No.: US 7,598,387 B2
(45) Date of Patent: Oct. 6, 2009

(54) SYNTHESIS OF ANTIDIABETIC ROSIGLITAZONE DERIVATIVES

(75) Inventors: Dharmaraj Ramachandra Rao, Maharashtra (IN); Rajendra Narayanrao Kankan, Maharashtra (IN)

(73) Assignee: Cipla Limited, Mumbai, Maharashtra (IN)

( * ) Notice: Subject to any disclaimer, the term of this patent is extended or adjusted under 35 U.S.C. 154(b) by 185 days.

(21) Appl. No.: 11/568,610

(22) PCT Filed: May 3, 2005

(86) PCT No.: PCT/GB2005/001671

§ 371 (c)(1),
(2), (4) Date: Jan. 11, 2007

(87) PCT Pub. No.: WO2005/105794

PCT Pub. Date: Nov. 10, 2005

(65) Prior Publication Data

US 2007/0191611 A1   Aug. 16, 2007

(30) Foreign Application Priority Data

May 5, 2004   (GB)   ................. 0410013.7

(51) Int. Cl.
*C07D 417/12*   (2006.01)
(52) U.S. Cl. ................................. 546/269.7
(58) Field of Classification Search ............... 546/269.7
See application file for complete search history.

(56) References Cited

FOREIGN PATENT DOCUMENTS

| EP | 0 306 228 A1 | 3/1989 |
|---|---|---|
| ES | 2 007 537 | 6/1989 |
| WO | WO 99/57123 A1 | 11/1999 |
| WO | WO 02/051823 A1 | 7/2002 |

OTHER PUBLICATIONS

Mueller, Eugen, "Hydrogen sulphite compounds of saturated aldehydes," Houben-Weyl Methoden der Organischen Chemie, vol. 2, No. 1, 1954, George Thieme Verlag, Stuttgart, De, pp. 482-488, XP-002320925.

Foreign communication from a related counterpart application—International Search Report, PCT/GB2005/001671, Aug. 16, 2005, 5 pages.

Foreign communication from a related counterpart application—International Preliminary Report on Patentability, PCT/GB2005/001671, Apr. 3, 2006, 6 pages.

*Primary Examiner*—Patricia L Morris
(74) *Attorney, Agent, or Firm*—Conley Rose, P.C.; Rodney B. Carroll

(57) ABSTRACT

A process of preparing rosiglitazone, or a pharmaceutically acceptable salt thereof, which process employs an intermediate metabisulphite complex of 4-[2-(N-methyl-N-(2-pyridyl)amino)ethoxy]benzaldehyde, which metabisulphite complex is represented by following formula (III):

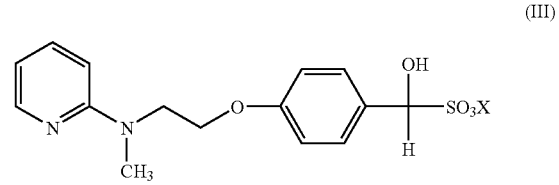

(III)

where X represents an alkali metal. The present invention further provides rosiglitazone, or a pharmaceutically acceptable salt thereof, prepared by the above process.

16 Claims, No Drawings

SYNTHESIS OF ANTIDIABETIC ROSIGLITAZONE DERIVATIVES

CROSS-REFERENCE TO RELATED APPLICATIONS

This application is a filing under 35 U.S.C. 371 of International Application No. PCT/GB2005/001671 filed May 3, 2005, entitled "Synthesis of Antidiabetic Rosiglitazone Derivatives," claiming priority of Great Britain Patent Application No. GB.0410013.7 filed May 5, 2004, which applications are incorporated by reference herein in their entirety.

FIELD OF THE INVENTION

The present invention describes a novel process for the synthesis of the antidiabetic compound, 5-[4-[2-(N-methyl-N-(2-pyridyl)amino)ethoxy]benzyl]thiazolidine-2,4-dione, namely rosiglitazone, especially as the maleate salt thereof, which is the preferred drug for non-insulin dependent diabetes mellitus (NIDDM).

BACKGROUND OF THE INVENTION

Rosiglitazone maleate, 5-[4-[2-(N-methyl-N-(2-pyridyl) amino)ethoxy]benzyl]thiazolidine-2,4-dione maleate, has the following general structural formula:

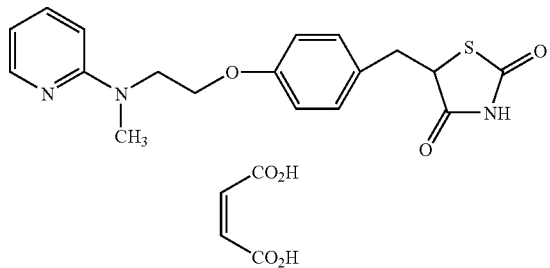

Rosiglitazone is a member of the thiazolidinedione class of compounds and is one of the most potent compounds of this class. The thiazolidinedione class of antidiabetics, such as pioglitazone, englitazone, rosiglitazone, troglitazone and ciglitazone, has been shown to alleviate insulin resistance in humans. Rosiglitazone is, therefore, a known antidiabetic compound, and more particularly is the preferred drug for non-insulin dependent diabetes mellitus (NIDDM). Diabetes mellitus is a complex, chronically progressive disease, which affects the function of the kidneys, eyes, vascular and nervous systems.

EP 0306228B describes the synthesis of 5-[4-[2-(N-methyl-N-(2-pyridyl)amino) ethoxy]benzylidene]thiazolidine-2,4-dione,

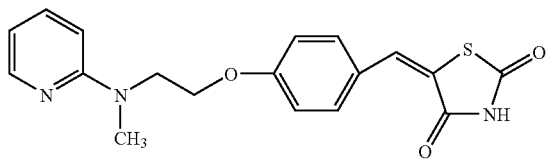

by condensing 4-[2-(N-methyl-N-(2-pyridyl)amino) ethoxy]benzaldehyde (which is an impure oil),

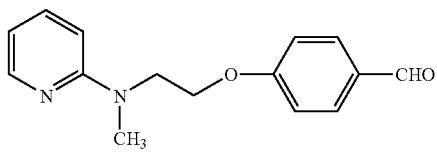

with 2,4-thiazolidinedione, to obtain above 5-[4-[2-(N-methyl-N-(2-pyridyl)amino) ethoxy]benzylidene]thiazolidine-2,4-dione, which is then reduced with Pd/C to obtain rosiglitazone free base. We have now developed an improved synthesis of rosiglitazone, or a pharmaceutically acceptable salt thereof, which alleviates many problems associated with the prior art preparation of rosiglitazone substantially as hereinafter described in greater detail.

SUMMARY OF THE INVENTION

According to the present invention, therefore, there is provided a process of preparing 5-[4-[2-(N-methyl-N-(2-pyridyl)amino)ethoxy]benzyl]thiazolidine-2,4-dione, namely rosiglitazone, of formula (I), or a pharmaceutically acceptable salt thereof, especially rosiglitazone maleate,

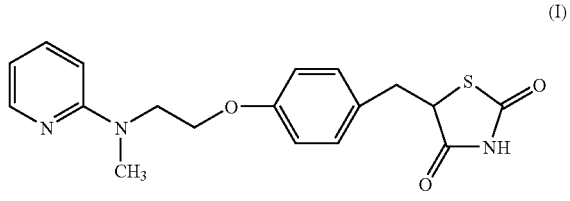

which process employs an intermediate metabisulphite complex of 4-[2-(N-methyl-N-(2-pyridyl)amino)ethoxy] benzaldehyde, which metabisulphite complex is represented by following formula (III)

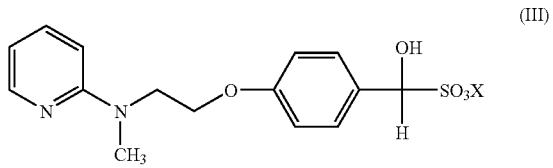

where X represents an alkali metal, such as sodium or potassium, especially sodium.

DETAILED DESCRIPTION OF THE INVENTION

According to a process of the present invention, a metabisulphite complex of formula (III) is converted to rosiglitazone free base, or a pharmaceutically acceptable salt thereof, by reacting the metabisulphite complex of formula (III) with thiazolidine 2,4 dione. Suitably, the reaction is carried out in toluene in the presence of a catalytic amount of piperidine and acetic acid. Alternatively, the reaction is carried out in a $C_{1-4}$ alcohol (preferably ethanol), or in a mixture of water and a $C_{1-4}$ alcohol, and at a temperature in the range of about 40° C. to about reflux temperature, preferably at about 80° C., in presence of an alkali or alkaline earth metal hydroxide, alkoxide or carboxylate, so as to yield a benzylidene intermediate of formula (II):

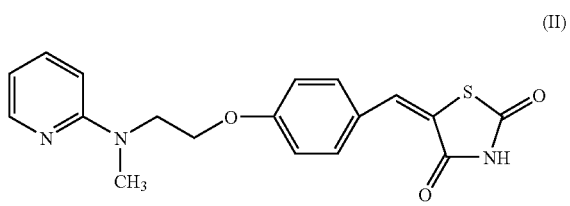

(II)

Benzylidene intermediate of formula (II) can be subsequently converted to rosiglitazone free base of formula (I) by appropriate reduction techniques, and optionally converting rosiglitazone free base to a pharmaceutically acceptable salt thereof, particularly rosiglitazone maleate. Suitable reducing techniques can comprise reduction in the presence of palladium on charcoal as described in EP 0306228B as referred to above. Alternatively, reduction can be carried out in the presence of a cobalt ion, a ligand and a reducing agent, wherein the cobalt ion is provided in the form of any of the following—cobaltous chloride, cobaltous diacetate and cobaltic chloride; the ligand is selected from the group consisting of dimethylglyoxime, 2,2'-bipyridyl and 1,10-phenanthroline; the reducing agent is selected from the group consisting of sodium borohydride, lithium borohydride, potassium borohydride, tetraalkylammonium borohydride and zinc borohydride; and optionally converting the thus formed rosiglitazone free base to a pharmaceutically acceptable salt thereof. Preferably the above reduction step is carried out in the presence of cobaltous chloride as the source of the cobalt ion, dimethylglyoxime as the ligand and sodium borohydride as the reducing agent.

A metabisulphite complex of formula (III) is suitably prepared by a process of the present invention from 4-[2-(N-methyl-N-(2-pyridyl)amino)ethoxy]benzaldehyde (known from the prior art as indicated above and referred to in the context of the present invention as an intermediate benzaldehyde compound of formula (IV)):

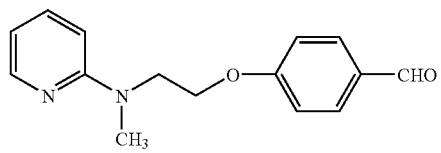

(IV)

by reacting the intermediate benzaldehyde compound of formula (IV) with an alkali metal metabisulphite salt, such as sodium or potassium metabisulphite, in particular sodium metabisulphite, in an aqueous solution comprising $C_{1-4}$ alcohols, typically at a temperature in the range of $-10°$ C. to reflux.

The prior art synthesis of 4-[2-(N-methyl-N-(2-pyridyl) amino)ethoxy]benzaldehyde has hitherto led to a number of in situ generated impurities, with the compound being prepared as a viscous oil and as such being difficult to isolate and purify. The purity of 4-[2-(N-methyl-N-(2-pyridyl)amino) ethoxy]benzaldehyde as prepared by prior art processes has generally not been more than about 50-55%. According to the present invention, however, 4-[2-(N-methyl-N-(2-pyridyl) amino)ethoxy]benzaldehyde is isolated and purified in the form of a solid metabisulphite complex of formula (III), which in addition to the associated improved purity obviates the handling properties of the viscous oil employed in the prior art reaction with thiazolidine 2,4 dione.

The present invention thus provides a process for the synthesis of 4-[2-(N-methyl-N-(2-pyridyl)amino)ethoxy]benzaldehyde, whereby the benzaldehyde forms an addition complex with an alkali metal metabisulphite salt, leading to the formation of metabisulphite complex of formula (III). This intermediate process step also provides means for purification of 4-[2-(N-methyl-N-(2-pyridyl)amino)ethoxy]benzaldehyde. A metabisulphite complex of formula (III) is a very fine crystalline solid in nature, having HPLC purity of about 96-99%, with a defined melting point making it easy to handle and as indicated above alleviating the prior art problems related to handling of viscous oils on an industrial scale.

Intermediate benzaldehyde compound of formula (IV) is in turn prepared from an intermediate compound of formula (V) in a process according to the present invention:

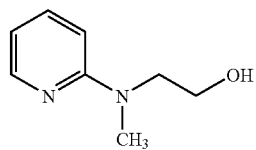

(V)

wherein intermediate compound of formula (V) and a 4-Hal benzaldehyde, where Hal represents bromo, chloro, fluoro or iodo, preferably fluoro, are dissolved in a polar aprotic solvent, preferably DMF, followed by sequential additions of sodium hydride in increasing molar quantities, suitably carried out at a temperature of below about 40° C., and subsequent stirring of the reaction mass at a temperature in the range of about 0 to 40° C., preferably at ambient temperature for a time period of not more than about 3 hrs. Intermediate benzaldehyde compound of formula (IV) isolated by this process has HPLC purity of more than about 80%.

4-[2-(N-methyl-N-(2-pyridyl)amino)ethoxy]benzaldehyde has hitherto been prepared by processes known in the art, for example by reaction of 2-(N-methyl-N-(2-pyridyl) amino) ethanol with 4-fluoro benzaldehyde in presence of sodium hydride. EP 0306228B discloses a process wherein sodium hydride is added to a stirred solution of 2-(N-methyl-N-(2-pyridyl)amino) ethanol in DMF followed by addition of 4-fluoro benzaldehyde and the reaction mixture was heated to 80° C. for 16 hrs. The crude viscous oil of 4-[2-(N-methyl-N-(2-pyridyl)amino)ethoxy]benzaldehyde was then isolated and purified by column chromatography. It has been seen that by following this prior art process, impurities were observed to an extent of about 30-40% and 4-[2-(N-methyl-N-(2-pyridyl)amino)ethoxy]benzaldehyde exhibited a purity not more than about 50-55%. As can be seen from the 80% purity of 4-[2-(N-methyl-N-(2-pyridyl)amino)ethoxy]benzaldehyde as prepared by a process according to the present invention, the present invention thus discloses an improvement in the process of preparing 4-[2-(N-methyl-N-(2-pyridyl) amino)ethoxy]benzaldehyde compared to the prior art.

It can be appreciated from the above that the present invention essentially provides modification of three process stages in the preparation of rosiglitazone, or a pharmaceutically acceptable salt thereof as follows.

According to the present invention, therefore, there is provided a process of preparing 5-[4-[2-(N-methyl-N-(2-pyridyl)amino)ethoxy]benzyl]thiazolidine-2,4-dione, namely rosiglitazone, of formula (I), or a pharmaceutically acceptable salt thereof, especially rosiglitazone maleate,

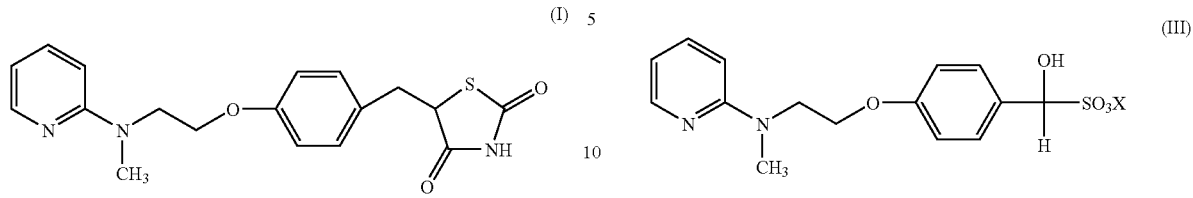

which process comprises reacting a metabisulphite complex of formula (III):

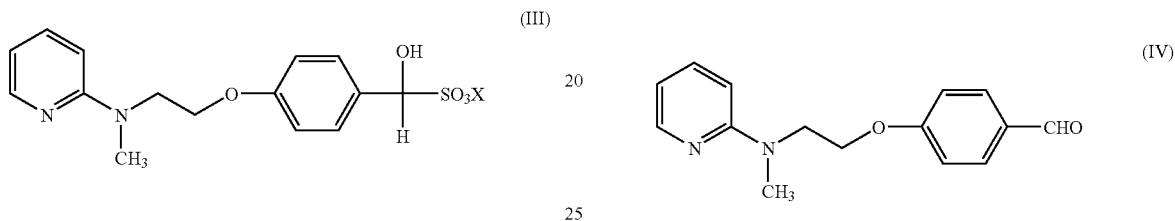

where X represents an alkali metal, such as sodium or potassium, especially sodium with thiazolidine 2,4 dione. Suitably, the reaction is carried out in toluene in the presence of a catalytic amount of piperidine and acetic acid. Alternatively, the reaction is carried out in a $C_{1-4}$ alcohol (preferably ethanol), or in a mixture of water and a $C_{1-4}$ alcohol, typically at a temperature in the range of about 40° C. to about reflux temperature, preferably at about 80° C., in presence of an alkali or alkaline earth metal hydroxide, alkoxide or carboxylate, so as to yield a benzylidene intermediate of formula (II):

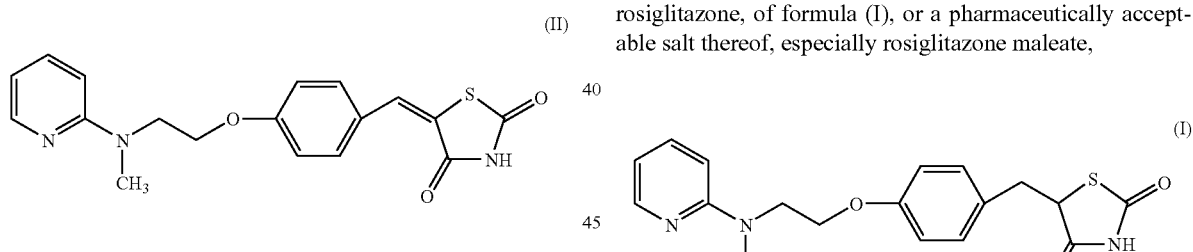

which can be subsequently converted to rosiglitazone free base of formula (I) by appropriate reduction techniques, and optionally converting rosiglitazone free base to a pharmaceutically acceptable salt thereof, particularly rosiglitazone maleate.

According to the present invention there is further provided a process of preparing 5-[4-[2-(N-methyl-N-(2-pyridyl)amino)ethoxy]benzyl]thiazolidine-2,4-dione, namely rosiglitazone, of formula (I), or a pharmaceutically acceptable salt thereof, especially rosiglitazone maleate,

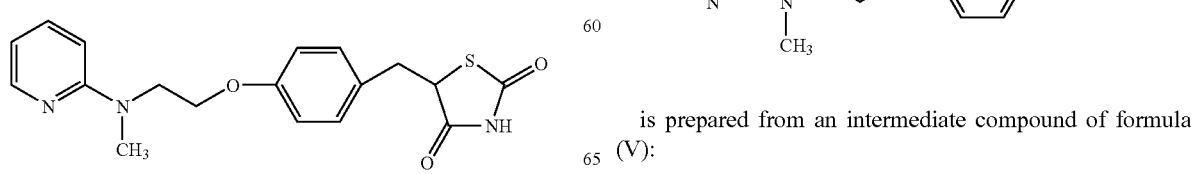

which process includes an intermediate process step wherein a metabisulphite complex of formula (III):

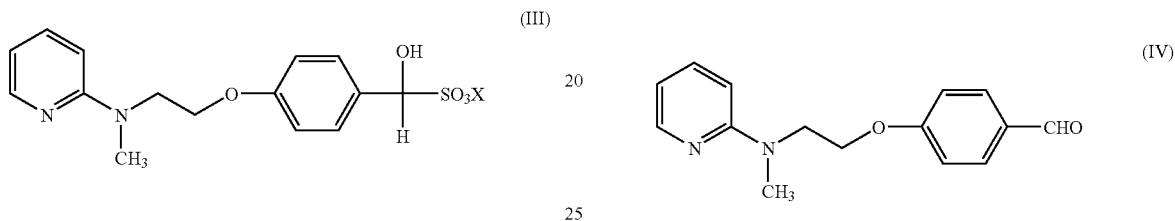

where X represents an alkali metal, such as sodium or potassium, especially sodium, is prepared from an intermediate benzaldehyde compound of formula (IV):

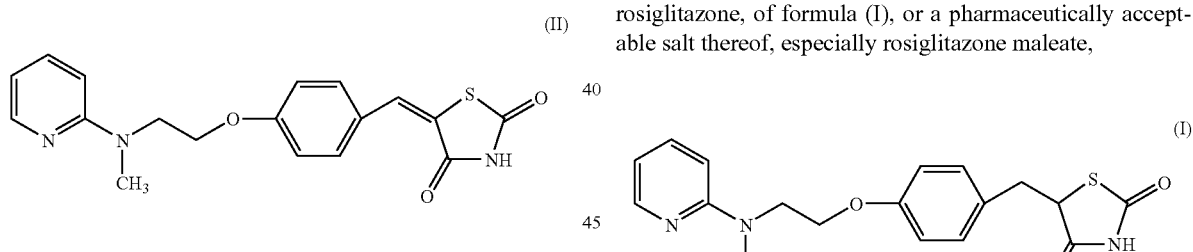

by reacting the intermediate benzaldehyde compound of formula (IV) with an alkali metal metabisulphite salt, such as sodium or potassium metabisulphite, in particular sodium metabisulphite, in an aqueous solution comprising $C_{1-4}$ alcohols, typically at a temperature in the range of −10° C. to reflux.

According to the present invention there is further provided a process of preparing 5-[4-[2-(N-methyl-N-(2-pyridyl)amino)ethoxy]benzyl]thiazolidine-2,4-dione, namely rosiglitazone, of formula (I), or a pharmaceutically acceptable salt thereof, especially rosiglitazone maleate,

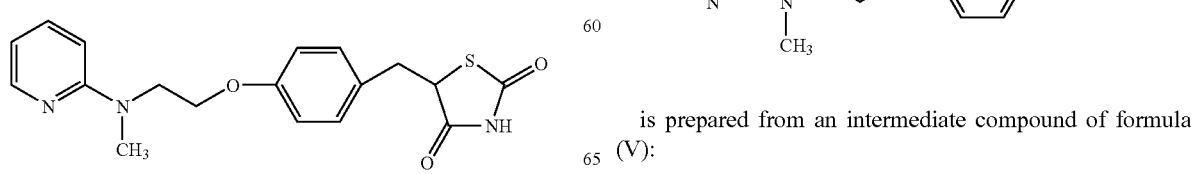

which process includes an intermediate process step wherein an intermediate benzaldehyde compound of formula (IV):

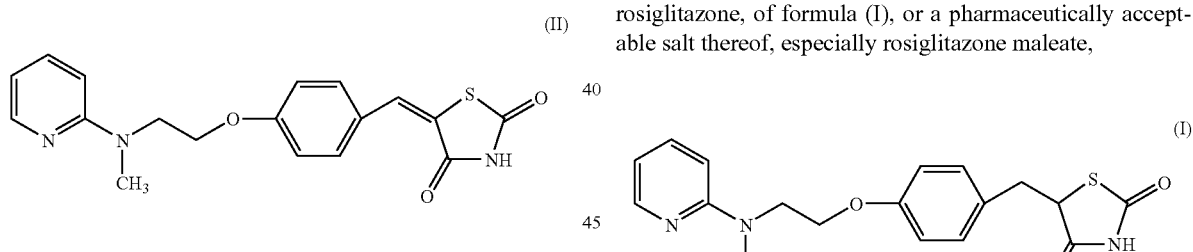

is prepared from an intermediate compound of formula (V):

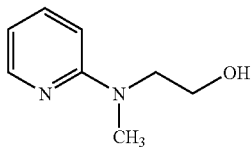

(V)

wherein intermediate compound of formula (V) and a 4-Hal benzaldehyde, where Hal represents bromo, chloro, fluoro or iodo, preferably fluoro, are dissolved in a polar aprotic solvent, preferably DMF, followed by sequential additions of sodium hydride in increasing molar quantities, suitably carried out at a temperature of below about 40° C., and subsequent stirring of the reaction mass at a temperature in the range of about 0 to 40° C., preferably at ambient temperature for a time period of not more than about 3 hrs.

There is still further provided by the present invention an overall process for the preparation of 5-[4-[2-(N-methyl-N-(2-pyridyl)amino)ethoxy]benzyl]thiazolidine-2,4-dione, namely rosiglitazone, of formula (I), or a pharmaceutically acceptable salt thereof, especially rosiglitazone maleate, which can be represented by the following reaction scheme:

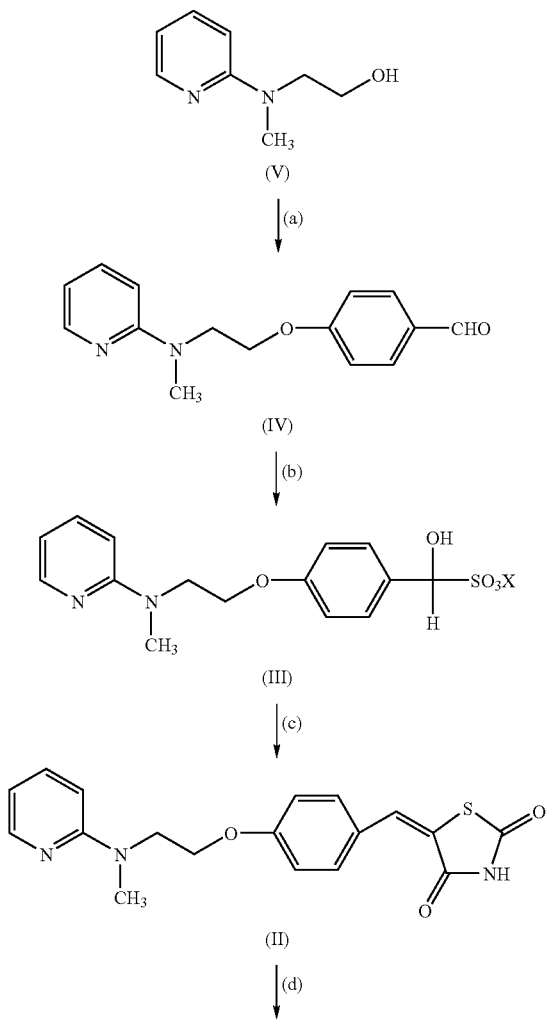

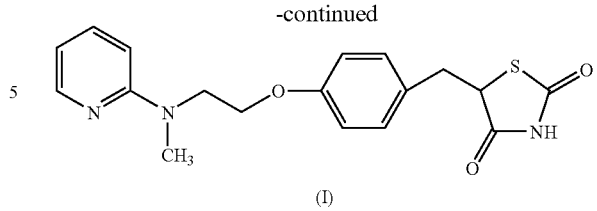

where X represents an alkali metal, such as sodium or potassium, especially sodium, wherein for intermediate process step (a) intermediate compound of formula (V) is reacted with a 4-Hal benzaldehyde, where Hal represents bromo, chloro, fluoro or iodo, preferably fluoro, dissolved in a polar aprotic solvent, preferably DMF, followed by sequential additions of sodium hydride in increasing molar quantities, suitably carried out at a temperature of below about 40° C., and subsequent stirring of the reaction mass at a temperature in the range of about 0 to 40° C., preferably at ambient temperature for a time period of not more than about 3 hrs; for intermediate process step (b) intermediate benzaldehyde compound of formula (IV) is reacted with an alkali metal metabisulphite salt, such as sodium or potassium metabisulphite, in particular sodium metabisulphite, in an aqueous solution comprising $C_{1-4}$ alcohols, typically at a temperature in the range of $-10°$ C. to reflux; for intermediate process step (c) a metabisulphite complex of formula (III) is reacted with thiazolidine 2,4 dione suitably either in toluene in the presence of a catalytic amount of piperidine and acetic acid, or in a $C_{1-4}$ alcohol (preferably ethanol), or in a mixture of water and a $C_{1-4}$ alcohol, typically at a temperature in the range of about 40° C. to about reflux temperature, preferably at about 80° C., in presence of an alkali or alkaline earth metal hydroxide, alkoxide or carboxylate; for intermediate process step (d) a benzylidene intermediate compound of formula (II) is converted to rosiglitazone free base of formula (I) by appropriate reduction techniques, and optionally converting rosiglitazone free base to a pharmaceutically acceptable salt thereof, particularly rosiglitazone maleate.

There is also provided by the present invention a metabisulphite complex of formula (III):

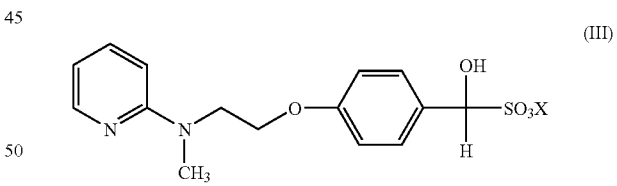

where X represents an alkali metal, such as sodium or potassium, especially sodium, and the use of this metabisulphite complex in the manufacture of rosiglitazone, or a pharmaceutically acceptable salt thereof.

The present invention further provides rosiglitazone free base, or a pharmaceutically acceptable salt thereof, prepared by a process as hereinbefore described.

Rosiglitazone free base, or a pharmaceutically acceptable salt thereof, as provided by the present invention, is useful in the treatment of Type II diabetes mellitus. Rosiglitazone as provided by the present invention can also be indicated to be of particular use for the treatment and/or prophylaxis of other diseases including hyperlipidaemia, hypertension and cardiovascular disease, especially atherosclerosis. In addition, rosiglitazone as provided by the present invention is considered to be useful for treating certain eating disorders, in particular the regulation of appetite and food intake in subjects suffering from disorders associated with under-eating, such as anorexia nervous, and disorders associated with over-eating, such as obesity and anorexia bulimia.

The present invention accordingly provides, therefore, for use in therapy rosiglitazone free base, or a pharmaceutically acceptable salt thereof, as provided by a process according to the present invention substantially as hereinbefore described.

Accordingly, the present invention provides for use in the treatment of and/or prophylaxis of hyperglycaemia, rosiglitazone free base, or a pharmaceutically acceptable salt thereof, as provided by a process according to the present invention. In particular, there is provided rosiglitazone free base, or a pharmaceutically acceptable salt thereof, as provided by a process according to the present invention for use in the treatment of diabetes mellitus.

The present invention further provides for use in the treatment and/or prophylaxis of hyperlipidaemia, rosiglitazone free base, or a pharmaceutically acceptable salt thereof, as provided by a process according to the present invention.

The present invention also further provides for use in the treatment of hypertension, cardiovascular disease and certain eating disorders, rosiglitazone free base, or a pharmaceutically acceptable salt thereof, as provided by a process according to the present invention. Cardiovascular disease includes in particular atherosclerosis. Certain eating disorders include in particular the regulation of appetite and food intake in, subjects suffering from disorders associated with under-eating, such as anorexia nervosa and disorders associated with over-eating, such as obesity and anorexia bulimia.

Accordingly, the present invention also provides a pharmaceutical composition comprising rosiglitazone free base, or a pharmaceutically acceptable salt thereof, as provided by a process according to the present invention, and a pharmaceutically acceptable carrier therefor. Preferably a composition as provided by the present invention can be for oral administration. The pharmaceutical compositions of the invention may, however, be administered in any suitable way and in any suitable form, for example orally in the form of tablets, capsules, liquid preparations, granules, lozenges, or parenterally in the form of injectable, or infusible, solutions or suspensions.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents can comprise: corn starch, potato starch, talcum, magnesium stearate, gelatine, lactose, gums, and the like. Any other adjuvant or additive colourings, aroma, preservatives or the like may also be used provided that they are compatible with the rosiglitazone as provided by the present invention.

Solutions for injections may be prepared by dissolving rosiglitazone as provided by the present invention and possible additives in a part of the solvent for injection, typically sterile water, adjusting the solution to the desired volume, sterilisation of the solution and filling in suitable ampoules or vials. Any suitable additive conventionally used in the art may be added, such as tonicity agents, preservatives, antioxidants and the like.

The present invention further provides a method for the treatment and/or prophylaxis of hyperglycaemia in a patient, which method comprises administering a therapeutically effective amount of rosiglitazone free base, or a pharmaceutically acceptable salt thereof, as provided by a process according to the present invention to a hyperglycaemic patient in need thereof. In particular, the present invention provides a method for the treatment and/or prophylaxis of diabetes mellitus in a patient, which method comprises administering a therapeutically effective amount of rosiglitazone free base, or a pharmaceutically acceptable salt thereof, as provided by a process according to the present invention to a patient suffering from, or susceptible to, diabetes mellitus.

The present invention further provides a method for the treatment of hyperlipidaemia in a patient, which comprises administering a therapeutically effective amount of rosiglitazone free base, or a pharmaceutically acceptable salt thereof, as provided by a process according to the present invention to a hyperlipidaemic patient in need thereof.

The present invention further provides a method for the treatment of hypertension, cardiovascular disease or certain eating disorders substantially as hereinbefore described, which comprises administering a therapeutically effective amount of rosiglitazone free base, or a pharmaceutically acceptable salt thereof, as provided by a process according to the present invention to a patient in need thereof.

In a further aspect, the present invention provides the use of rosiglitazone free base, or a pharmaceutically acceptable salt thereof, as provided by a process according to the present invention, for the manufacture of a medicament for the treatment and/or prophylaxis of hyperglycaemia. In particular, the present invention provides use of rosiglitazone free base, or a pharmaceutically acceptable salt thereof, as provided by a process according to the present invention for the manufacture of a medicament for the treatment and/or prophylaxis of diabetes mellitus.

The present invention also provides the use of rosiglitazone free base, or a pharmaceutically acceptable salt thereof, as provided by a process according to the present invention for the manufacture of a medicament for the treatment and/or prophylaxis of hyperlipidaemia.

The present invention also provides the use of rosiglitazone free base, or a pharmaceutically acceptable salt thereof, as provided by a process according to the present invention for the manufacture of a medicament for the treatment and/or prophylaxis of hypertension, cardiovascular disease or certain eating disorders.

The particular dosage form of rosiglitazone as provided by the present invention required for therapeutic use or treatment in accordance with the present invention will depend on the particular disease state being treated, and the symptoms and severity thereof. Dosage, routes of administration, and frequency of dosing are best decided by an attending physician.

The present invention will now be further illustrated by the following Examples, which do not limit the scope of the invention in any way.

EXAMPLES

Example 1

Preparation of 4-(2-(N-methyl-N-(2-pyridyl)amino-ethoxy)benzaldehyde 2-(N-methyl-N-(2-pyridyl)amino ethanol (50 gms, 0.32M) and 4-fluoro benzaldehyde (68 gms, 0.547M) were dissolved in DMF (500 ml) and sodium hydride (2 gms) was added. The reaction mass was stirred for 15 minutes and the temperature was maintained below 35° C. Sodium hydride (4 gms) was added again and the reaction mass stirred for 15 minutes. Subsequently 8 and 10 gms of sodium hydride were sequentially added at 15 minute intervals. The reaction was monitored by HPLC. After completion of reaction, the reaction mass was cooled to 5° C., and methanol (30 ml) was added slowly. The reaction mass was then quenched into water (approx 21 trs) and extracted with ethyl acetate (4×500 ml). The combined organic layers were washed with water (6×500 ml). The organic layer was dried over sodium sulphate and concentrated to obtain the title compound as an oil (105 gms, 84% HPLC purity).

Example 2

Preparation of 4-[2-(N-methyl-N-(2-pyridyl)amino) ethoxy]benzaldehyde sodium metabisulphite complex 4-[2-(N-methyl-N-(2-pyridyl)amino)ethoxy]benzaldehyde (10 gms, 0.039M) was stirred with industrial spirit (150 ml) and cooled to 15° C. A solution of sodium metabisulphite (11 gms, 0.057M) in water (20 ml) was added drop wise to the above solution over a time period of about 15 to 20 minutes, whilst maintaining the temperature below about 20° C. The reaction mixture was further cooled to 10° C. and stirred for 1 to 2 hours. The resulting precipitate was then filtered and washed with industrial spirit (25 ml×2) followed by water (25 ml). The solid obtained was then dried in a vacuum oven at 40° C. to obtain the title complex (10 gms, HPLC purity 98.5%).

Example 3

Preparation of 4-[2-(N-methyl-N-(2-pyridyl)amino) ethoxy]benzaldehyde sodium metabisulphite complex 4-[2-(N-methyl-N-(2-pyridyl)amino)ethoxy]benzaldehyde (20 gms, 84% HPLC purity) was stirred with methanol (200 ml) and cooled to 15° C. A solution of sodium metabisulphite (22 gms, 0.115M) in water (40 ml) was added drop wise to the above solution over a time period of about 15 to 20 minutes, whilst maintaining the temperature below about 20° C. The reaction mixture was then cooled to 10° C. and stirred for about 2 hours. The resulting solid precipitate was then filtered and washed with methanol (25 ml) and water (25 ml). The solid was then dried in a vacuum oven at 40° C. to obtain the title compound (20 gms, 98% HPLC purity).

Example 4

Preparation of 5-(4-[2-(N-methyl-N-(2-pyridyl) aminoethoxy]benzylidene)-2,4-thiazolidinedione 4-[2-(N-methyl-N-(2-pyridyl)amino)ethoxy]benzaldehyde sodium metabisulphite complex (10 gms, 0.027M) from Example 3 was suspended in toluene (100 ml) with 2,4-thiazolidine dione (3.2 gms, 0.0273M) at ambient temperature. A catalytic amount of piperidine (0.2 ml) and acetic acid (0.1 ml) was added to the reaction mixture under stirring. The reaction mass was then refluxed using Dean stark apparatus for 5 to 6 hours. The reaction mass was then cooled to 60° C. and concentrated to half of its volume under vacuum. Methanol (50 ml) was added drop wise to the reaction mass at 60° C. and cooled gradually to room temperature. The suspension was stirred at room temperature for about 2 hours and the solid filtered and washed with methanol (25 ml), followed by water (200 ml). The resulting solid was then dried under vacuum oven at 60° C. to obtain the title compound (6.5 gms, 98% HPLC purity).

Example 5

Preparation of 5-(4-[2-(N-methyl-N-(2-pyridyl)aminoethoxy]benzylidene)-2,4-thiazolidinedione 4-[2-(N-methyl-N-(2-pyridyl)amino)ethoxy]benzaldehyde sodium metabisulphite complex (10 gms, 0.027M) from Example 3 was suspended in industrial spirit (150 ml) with 2,4-thiazolidine dione (6.4 gms, 0.0546M) at ambient temperature. Sodium hydroxide pellets (6.0 gms 0.15 moles) were added to the reaction mixture under stirring. The reaction mass was then refluxed for 18 hours, the reaction mass was then cooled to 0° C. and neutralized with (1:1) hydrochloric acid water mixture. The suspension was stirred at 10° C. for 1 hour. The solid was filtered and washed with demineralised water (50 ml). The resulting solid was then dried under vacuum oven at 60° C. to obtain the title compound (9 gms, 98% HPLC purity).

Example 6

Preparation of 5-(4-[2-(N-methyl-N-(2-pyridyl)aminoethoxy]benzyl)-2,4-thiazolidinedione (in Accordance with EP 0306228B)

5-(4-[2-(N-methyl-N-(2-pyridyl)aminoethoxy]benzylidene)-2,4-thiazolidinedione (20 gms) in dry 1,4-dioxane (700 ml) was reduced under hydrogen in the presence of 10% Palladium on charcoal (30 gms) at ambient temperature and atmospheric pressure until hydrogen uptake was ceased. The reaction mass was filtered through celite. The clear filtrate was evaporated to dryness under vacuum. The product obtained was crystallized from methanol.

Example 7

Preparation of 5-(4-[2-(N-methyl-N-(2-pyridyl)aminoethoxy]benzyl)-2,4-thiazolidinedione 5-(4-[2-(N-methyl-N-(2-pyridyl)aminoethoxy]benzylidene)-2,4-thiazolidinedione (10 gms) was suspended in water (30 ml) and tertahydrofuran (30 ml), and to this suspension was added 4% sodium hydroxide (25 ml). The resulting mixture was cooled to 10° C. and to this was added a catalyst solution prepared by dissolving dimethyl glyoxime (1.88 gms) and cobaltous chloride (0.200 gms) in tetrahydrofuran (30 ml). Then a solution of sodium borohydride (3.2 gms) in water (30 ml), and 4% sodium hydroxide (9.4 ml), was slowly added at 10° C. over a period of 90 minutes. The resulting reaction mixture was stirred at 25° C. for 16 hours and later was acidified with 60% glacial acetic acid, which was added very slowly over a period of 1-2 hours. The resulting suspension was further stirred for 1.5 hours. The solid obtained was filtered and washed with water and dried under vacuum at 60° C. to obtain 9.3 gms of 5-(4-[2-(N-methyl-N-(2-pyridyl) aminoethoxy]benzyl)-2,4-thiazolidinedione (rosiglitazone free base).

The invention claimed is:

1. A process of preparing rosiglitazone of formula (I), or a pharmaceutically acceptable salt thereof,

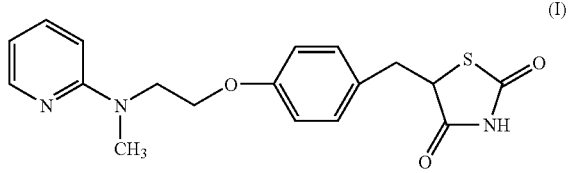

comprising reacting a thiazolidine 2,4 dione and an intermediate metabisulphite complex of 4-[2-(N-methyl-N-(2-pyridyl)amino)ethoxy]benzaldehyde, which metabisulphite complex is represented by following formula (III):

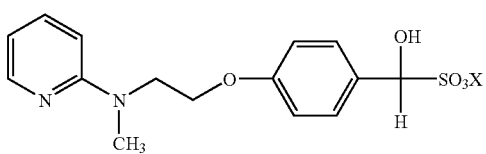

where X represents an alkali metal.

2. A process according to claim 1, wherein X is sodium or potassium.

3. A process according to claim 2, wherein X is sodium.

4. A process according to claim 1, wherein said metabisulphite complex of formula (III) is reacted with the thiazolidine 2,4 dione in toluene in the presence of a catalytic amount of piperidine and acetic acid.

5. A process according to claim 1, wherein said metabisulphite complex of formula (III) is reacted with the thiazolidine 2,4 dione in a $C_{1-4}$ alcohol or in a mixture of water and a $C_{1-4}$ alcohol.

6. A process according to claim 5, wherein said $C_{1-4}$ alcohol is ethanol.

7. A process according to claim 5, wherein said metabisulphite complex of formula (III) is reacted with the thiazolidine 2,4 dione at a temperature in the range of about 40° C. to about reflux temperature.

8. A process according to claim 7, wherein said temperature is about 80° C.

9. A process according to claim 5, wherein said metabisulphite complex of formula (III) is reacted with the thiazolidine 2,4 dione in the presence of an alkali or alkaline earth metal hydroxide, alkoxide or carboxylate.

10. A process according to claim 1, wherein said metabisulphite complex of formula (III) is reacted with the thiazolidine 2,4 dione so as to yield a benzylidene intermediate of formula (II):

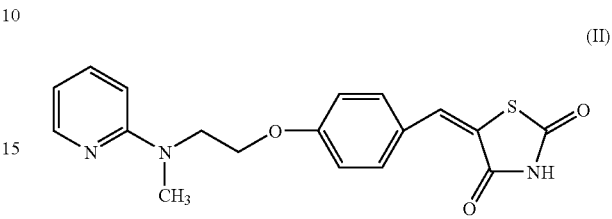

which is subsequently reduced to yield rosiglitazone free base of formula (I), and optionally reacting rosiglitazone free base with an acid to form a pharmaceutically acceptable salt of rosiglitazone.

11. A process according to claim 10, wherein said metabisulphite complex of formula (III) is reacted with the thiazolidine 2,4 dione in toluene in the presence of a catalytic amount of piperidine and acetic acid.

12. A process according to claim 10, wherein said metabisulphite complex of formula (III) is reacted with the thiazolidine 2,4 dione in a $C_{1-4}$ alcohol or in a mixture of water and a $C_{1-4}$ alcohol.

13. A process according to claim 12, wherein said $C_{1-4}$ alcohol is ethanol.

14. A process according to claim 12, wherein said metabisulphite complex of formula (III) is reacted with the thiazolidine 2,4 dione at a temperature in the range of about 40° C. to about reflux temperature.

15. A process according to claim 14, wherein said temperature is about 80° C.

16. A process according to claim 12, wherein said metabisulphite complex of formula (III) is reacted with the thiazolidine 2,4 dione in the presence of an alkali or alkaline earth metal hydroxide, alkoxide or carboxylate.

* * * * *